(12) United States Patent
Olhava et al.

(10) Patent No.: US 8,003,819 B2
(45) Date of Patent: *Aug. 23, 2011

(54) PROTEASOME INHIBITORS

(75) Inventors: Edward J. Olhava, Newton, MA (US); Mihaela Diana Danca, Mendham, NJ (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/704,830

(22) Filed: Feb. 12, 2010

(65) Prior Publication Data

US 2010/0204180 A1 Aug. 12, 2010

Related U.S. Application Data

(63) Continuation of application No. 12/217,243, filed on Jul. 2, 2008, now Pat. No. 7,687,662, which is a continuation of application No. 11/890,412, filed on Aug. 6, 2007, now Pat. No. 7,442,830.

(51) Int. Cl.
| | |
|---|---|
| C07F 5/02 | (2006.01) |
| C07C 229/00 | (2006.01) |
| C07C 233/00 | (2006.01) |
| C07C 239/00 | (2006.01) |
| C07C 235/00 | (2006.01) |
| A61K 31/69 | (2006.01) |

(52) U.S. Cl. ............ 562/7; 562/450; 564/8; 564/169; 514/64

(58) Field of Classification Search ............ 562/7, 450; 564/8, 169; 514/64
See application file for complete search history.

(56) References Cited

U.S. PATENT DOCUMENTS

| | | | |
|---|---|---|---|
| 4,499,082 | A | 2/1985 | Shenvi et al. |
| 5,159,060 | A | 10/1992 | Kinder et al. |
| 5,580,486 | A | 12/1996 | Labeque et al. |
| 6,060,462 | A | 5/2000 | Galemmo, Jr. et al. |
| 7,442,830 | B1 | 10/2008 | Olhava et al. |
| 2005/0107307 | A1 | 5/2005 | Bernadini et al. |

FOREIGN PATENT DOCUMENTS

| | | |
|---|---|---|
| WO | WO 96/13266 A1 | 5/1990 |
| WO | WO 02/059131 A1 | 8/2002 |
| WO | WO 03/059898 A2 | 7/2003 |
| WO | WO 2005/097809 A2 | 10/2005 |
| WO | WO 2007/005991 A1 | 1/2007 |

OTHER PUBLICATIONS

Kinder, David H., et al., "Acylamino boronic acids and difluoroborane analogues of amino acids: potent inhibitors of chymotrypsin and elastase," *Journal of Medicinal Chemistry*, vol. 28, No. 12 (1985) pp. 1917-1925.

Tran, Thuy, et al., "Synthesis and structure-activity relationship of N-acyl-Gly-, N-acyl-Sar- and N-blocked-boroPro inhibitors of FAP, DPP4, and POP," *Bioorganic & Medicinal Chemistry Letters*, vol. 17 (2007) pp. 1438-1442.

International Search Report and Written Opinion dated Dec. 3, 2007 in International Application No. PCT/US07/017440 which corresponds with U.S. Appl. No. 11/890,412.

Gardner, Robert C., et al., "Characterization of peptidyl boronic acid inhibitors of mammalian 20 S and 26 S proteasomes and their inhibition of proteasomes in cultured cells," *Biochemistry*, vol. 346 (2000) pp. 447-454.

Kisselev, Alexei F., et al., "Proteasome inhibitors: from research tools to drug candidates," *Chemistry & Biology*, vol. 8, No. 8 (2001) pp. 739-758.

Loidl, Gunther, et al., "Bifunctional inhibitors of the trypsin-like activity of eukaryotic proteasomes," *Chemistry & Biology*, vol. 6, No. 4 (1999) pp. 197-204.

*Primary Examiner* — Sikarl Witherspoon

(57) ABSTRACT

The present invention provides novel compounds useful as proteasome inhibitors. The invention also provides pharmaceutical compositions comprising the compounds of the invention and methods of using the compositions in the treatment of various diseases.

3 Claims, No Drawings

PROTEASOME INHIBITORS

RELATED APPLICATIONS

This application is a continuation of U.S. patent application Ser. No. 12/217,243, filed on Jul. 2, 2008 now U.S. Pat. No. 7,687,662, which is a continuation of U.S. patent application Ser. No. 11/890,412, filed on Aug. 6, 2007, now U.S. Pat. No. 7,442,830 B1, each of which applications is hereby incorporated by reference in its entirety.

FIELD OF THE INVENTION

The present invention relates to boronic acid and boronic ester compounds useful as proteasome inhibitors. The invention also provides pharmaceutical compositions comprising the compounds of the invention and methods of using the compositions in the treatment of various diseases.

BACKGROUND OF THE INVENTION

Boronic acid and ester compounds display a variety of pharmaceutically useful biological activities. Shenvi et al., U.S. Pat. No. 4,499,082 (1985), discloses that peptide boronic acids are inhibitors of certain proteolytic enzymes. Kettner and Shenvi, U.S. Pat. No. 5,187,157 (1993), U.S. Pat. No. 5,242,904 (1993), and U.S. Pat. No. 5,250,720 (1993), describe a class of peptide boronic acids that inhibit trypsin-like proteases. Kleeman et al., U.S. Pat. No. 5,169,841 (1992), discloses N-terminally modified peptide boronic acids that inhibit the action of renin. Kinder et al., U.S. Pat. No. 5,106,948 (1992), discloses that certain boronic acid compounds inhibit the growth of cancer cells. Bachovchin et al., WO 07/0005991, discloses peptide boronic acid compounds that inhibit fibroblast activating protein.

Boronic acid and ester compounds hold particular promise as inhibitors of the proteasome, a multicatalytic protease responsible for the majority of intracellular protein turnover. Adams et al., U.S. Pat. No. 5,780,454 (1998), describes peptide boronic ester and acid compounds useful as proteasome inhibitors. The reference also describes the use of boronic ester and acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, and to inhibit NF-κB dependent cell adhesion. Furet et al., WO 02/096933, Chatterjee et al., WO 05/016859, and Bernadini et al, WO 05/021558 and WO 06/08660, disclose additional boronic ester and acid compounds that are reported to have proteasome inhibitory activity.

Ciechanover, *Cell*, 79: 13-21 (1994), discloses that the proteasome is the proteolytic component of the ubiquitin-proteasome pathway, in which proteins are targeted for degradation by conjugation to multiple molecules of ubiquitin. Ciechanover also discloses that the ubiquitin-proteasome pathway plays a key role in a variety of important physiological processes. Rivett et al., *Biochem. J.* 291:1 (1993) discloses that the proteasome displays tryptic-, chymotryptic-, and peptidylglutamyl peptidase activities. Constituting the catalytic core of the 26S proteasome is the 20S proteasome. McCormack et al., *Biochemistry* 37:7792 (1998), teaches that a variety of peptide substrates, including Suc-Leu-Leu-Val-Tyr-AMC, Z-Leu-Leu-Arg-AMC, and Z-Leu-Leu-Glu-2NA, wherein Suc is N-succinyl, AMC is 7-amino-4-methylcoumarin, and 2NA is 2-naphthylamine, are cleaved by the 20S proteasome.

Proteasome inhibition represents an important new strategy in cancer treatment. King et al., *Science* 274:1652-1659 (1996), describes an essential role for the ubiquitin-proteasome pathway in regulating cell cycle, neoplastic growth and metastasis. The authors teach that a number of key regulatory proteins, including, cyclins, and the cyclin-dependent kinases p21 and p27$^{KIP1}$, are temporally degraded during the cell cycle by the ubiquitin-proteasome pathway. The ordered degradation of these proteins is required for the cell to progress through the cell cycle and to undergo mitosis.

Furthermore, the ubiquitin-proteasome pathway is required for transcriptional regulation. Palombella et al., *Cell*, 78:773 (1994), teaches that the activation of the transcription factor NF-κB is regulated by proteasome-mediated degradation of the inhibitor protein IκB. In turn, NF-κB plays a central role in the regulation of genes involved in the immune and inflammatory responses. Read et al., *Immunity* 2:493-506 (1995), teaches that the ubiquitin-proteasome pathway is required for expression of cell adhesion molecules, such as E-selectin, ICAM-1, and VCAM-1. Zetter, *Seminars in Cancer Biology* 4:219-229 (1993), teaches that cell adhesion molecules are involved in tumor metastasis and angiogenesis in vivo, by directing the adhesion and extravastation of tumor cells to and from the vasculature to distant tissue sites within the body. Moreover, Beg and Baltimore, *Science* 274:782 (1996), teaches that NF-κB is an anti-apoptotic controlling factor, and inhibition of NF-κB activation makes cells more sensitive to environmental stress and cytotoxic agents.

The proteasome inhibitor VELCADE® (bortezomib; N-2-pyrazinecarbonyl-L-phenylalanine-L-leucineboronic acid) is the first proteasome inhibitor to achieve regulatory approval. Mitsiades et al., *Current Drug Targets*, 7:1341 (2006), reviews the clinical studies leading to the approval of bortezomib for the treatment of multiple myeloma patients who have received at least one prior therapy. Fisher et al., *J. Clin. Oncol.*, 30:4867, describes an international multi-center Phase II study confirming the activity of bortezomib in patients with relapsed or refractory mantle cell lymphoma. Ishii et al., *Anti-Cancer Agents in Medicinal Chemistry*, 7:359 (2007), and Roccaro et al., *Curr. Pharm. Biotech.*, 7:1341 (2006), discuss a number of molecular mechanisms that may contribute to the antitumor activities of bortezomib.

As evidenced by the above references, the proteasome represents an important target for therapeutic intervention. There is thus a continuing need for new and/or improved proteasome inhibitors.

DESCRIPTION OF THE INVENTION

The present invention provides compounds that are effective inhibitors of the proteasome. These compounds are useful for inhibiting proteasome activity in vitro and in vivo, and are especially useful for the treatment of various cell proliferative diseases.

Compounds of the invention are of the general formula (I):

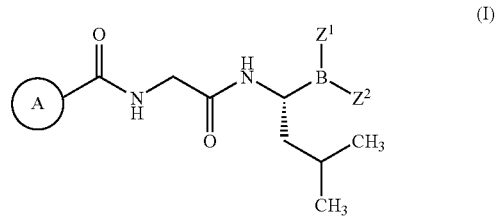

(I)

or a pharmaceutically acceptable salt or boronic acid anhydride thereof, wherein:

Z¹ and Z² are each independently hydroxy, alkoxy, aryloxy, or aralkoxy; or Z¹ and Z² together form a moiety derived from a boronic acid complexing agent; and Ring A is selected from the group consisting of

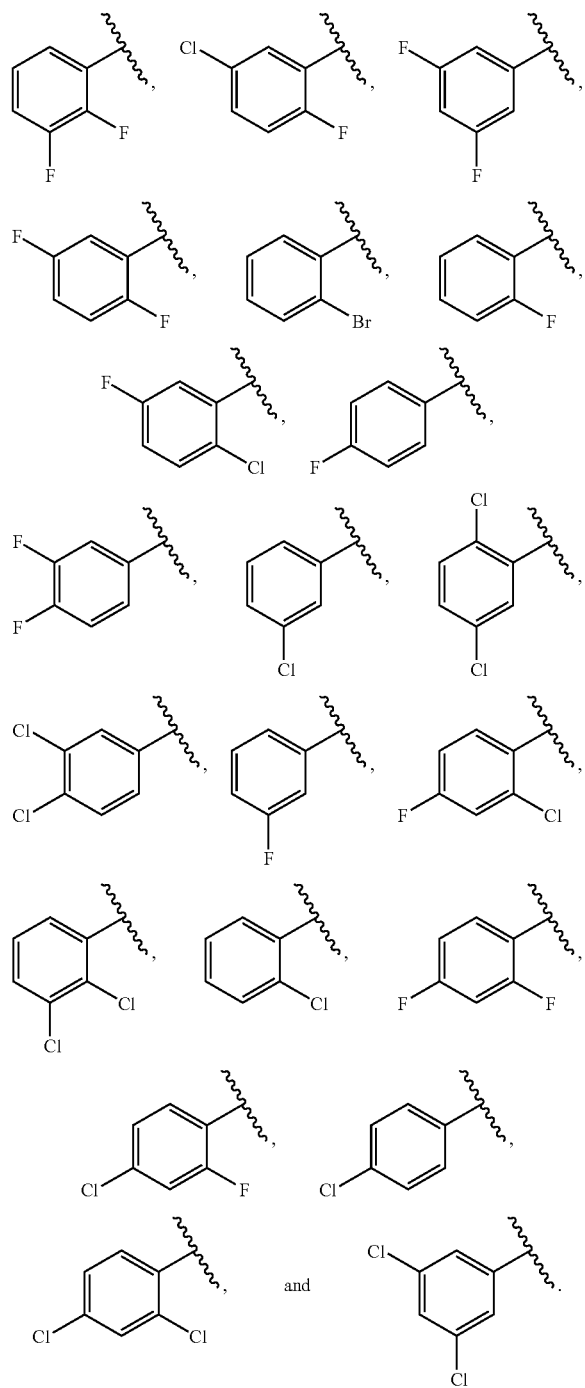

Boronic acid compounds of formula (I), wherein Z¹ and Z² are each hydroxy, are referred to by the following chemical names:

TABLE 1

Proteasome Inhibitors

| | Chemical Name |
|---|---|
| I-1 | [(1R)-1-({[(2,3-difluorobenzoyl)amino]acetyl}amino)-3-methylbutyl]boronic acid |
| I-2 | [(1R)-1-({[(5-chloro-2-fluorobenzoyl)amino]acetyl}amino)-3-methylbutyl]boronic acid |
| I-3 | [(1R)-1-({[(3,5-difluorobenzoyl)amino]acetyl}amino)-3-methylbutyl]boronic acid |
| I-4 | [(1R)-1-({[(2,5-difluorobenzoyl)amino]acetyl}amino)-3-methylbutyl]boronic acid |
| I-5 | [(1R)-1-({[(2-bromobenzoyl)amino]acetyl}amino)-3-methylbutyl]boronic acid |
| I-6 | [(1R)-1-({[(2-fluorobenzoyl)amino]acetyl}amino)-3-methylbutyl]boronic acid |
| I-7 | [(1R)-1-({[(2-chloro-5-fluorobenzoyl)amino]acetyl}amino)-3-methylbutyl]boronic acid |
| I-8 | [(1R)-1-({[(4-fluorobenzoyl)amino]acetyl}amino)-3-methylbutyl]boronic acid |
| I-9 | [(1R)-1-({[(3,4-difluorobenzoyl)amino]acetyl}amino)-3-methylbutyl]boronic acid |
| I-10 | [(1R)-1-({[(3-chlorobenzoyl)amino]acetyl}amino)-3-methylbutyl]boronic acid |
| I-11 | [(1R)-1-({[(2,5-dichlorobenzoyl)amino]acetyl}amino)-3-methylbutyl]boronic acid |
| I-12 | [(1R)-1-({[(3,4-dichlorobenzoyl)amino]acetyl}amino)-3-methylbutyl]boronic acid |
| I-13 | [(1R)-1-({[(3-fluorobenzoyl)amino]acetyl}amino)-3-methylbutyl]boronic acid |
| I-14 | [(1R)-1-({[(2-chloro-4-fluorobenzoyl)amino]acetyl}amino)-3-methylbutyl]boronic acid |
| I-15 | [(1R)-1-({[(2,3-dichlorobenzoyl)amino]acetyl}amino)-3-methylbutyl]boronic acid |
| I-16 | [(1R)-1-({[(2-chlorobenzoyl)amino]acetyl}amino)-3-methylbutyl]boronic acid |
| I-17 | [(1R)-1-({[(2,4-difluorobenzoyl)amino]acetyl}amino)-3-methylbutyl]boronic acid |
| I-18 | [(1R)-1-({[(4-chloro-2-fluorobenzoyl)amino]acetyl}amino)-3-methylbutyl]boronic acid |
| I-19 | [(1R)-1-({[(4-chlorobenzoyl)amino]acetyl}amino)-3-methylbutyl]boronic acid |
| I-20 | [(1R)-1-({[(2,4-dichlorobenzoyl)amino]acetyl}amino)-3-methylbutyl]boronic acid |
| I-21 | [(1R)-1-({[(3,5-dichlorobenzoyl)amino]acetyl}amino)-3-methylbutyl]boronic acid |

The term "alkyl", used alone or as part of a larger moiety, refers to a straight or branched chain or cyclic aliphatic group having from 1 to 12 carbon atoms. The term "alkoxy" refers to an —O-alkyl radical.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$aryl($C_{1-3}$)alkyl, including, without limitation, benzyl, phenethyl, and naphthylmethyl.

The term "substituted", as used herein, means that a hydrogen radical of the designated moiety is replaced with the radical of a specified substituent, provided that the substitution results in a stable or chemically feasible compound. Nonlimiting examples of suitable substituents include $C_{1-6}$ alkyl, $C_{3-8}$ cycloalkyl, $C_{1-6}$alkyl($C_{3-8}$)cycloalkyl, $C_{2-8}$ alkenyl, $C_{2-8}$ alkynyl, cyano, amino, $C_{1-6}$ alkylamino, di($C_{1-6}$) alkylamino, benzylamino, dibenzylamino, nitro, carboxy, carbo($C_{1-6}$)alkoxy, trifluoromethyl, halogen, $C_{1-6}$ alkoxy, $C_{6-10}$ aryl, $C_{6-10}$ aryl($C_{1-6}$)alkyl, $C_{6-10}$ aryl($C_{1-6}$)alkoxy, hydroxy, $C_{1-6}$ alkylthio, $C_{1-6}$ alkylsulfinyl, $C_{1-6}$ alkylsulfonyl, $C_{6-10}$ arylthio, $C_{6-10}$ arylsulfinyl, $C_{6-10}$ arylsulfonyl, $C_{6-10}$ aryl, $C_{1-6}$ alkyl($C_{6-10}$)aryl, and halo($C_{6-10}$)aryl.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used herein, the term "boronic acid" refers to a chemical compound containing a —B(OH)$_2$ moiety. In some embodiments, boronic acid compounds can form oligomeric anhydrides by dehydration of the boronic acid moiety. For example, Snyder et al., *J. Am. Chem. Soc.* 80:3611 (1958), reports oligomeric arylboronic acids.

As used herein, the term "boronic acid anhydride" refers to a chemical compound formed by combination of two or more molecules of a boronic acid compound, with loss of one or more water molecules. When mixed with water, the boronic acid anhydride compound is hydrated to release the free boronic acid compound. In various embodiments, the boronic acid anhydride can comprise two, three, four, or more boronic acid units, and can have a cyclic or linear configuration. Non-limiting examples of oligomeric boronic acid anhydrides of peptide boronic acids compound of the invention are illustrated below:

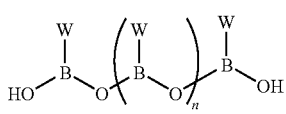

(1)

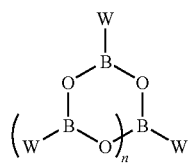

(2)

In formulae (1) and (2), the variable n is an integer from 0 to about 10, preferably 0, 1, 2, 3, or 4. In some embodiments, the boronic acid anhydride compound comprises a cyclic trimer ("boroxine") of formula (2), wherein n is 1. The variable W has the formula (3):

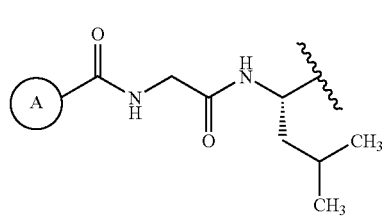

(3)

wherein Ring A has the values described above for formula (I).

In some embodiments, at least 80% of the boronic acid present in the boronic acid anhydride compound exists in a single oligomeric anhydride form. In some embodiments, at least 85%, 90%, 95%, or 99% of the boronic acid present in the boronic acid anhydride compound exists in a single oligomeric anhydride form. In certain preferred embodiments, the boronic acid anhydride compound consists of, or consists essentially of, a boroxine having formula (3).

The boronic acid anhydride compound preferably can be prepared from the corresponding boronic acid by exposure to dehydrating conditions, including, but not limited to, recrystallization, lyophilization, exposure to heat, and/or exposure to a drying agent. Nonlimiting examples of suitable recrystallization solvents include ethyl acetate, dichloromethane, hexanes, ether, acetonitrile, ethanol, and mixtures thereof.

In some embodiments, $Z^1$ and $Z^2$ together form a moiety derived from a boronic acid complexing agent. For purposes of the invention, the term "boronic acid complexing agent" refers to any compound having at least two functional groups, each of which can form a covalent bond with boron. Nonlimiting examples of suitable functional groups include amino and hydroxyl. In some embodiments, at least one of the functional groups is a hydroxyl group. The term "moiety derived from a boronic acid complexing agent" refers to a moiety formed by removing the hydrogen atoms from two functional groups of a boronic acid complexing agent.

As used herein, the terms "boronate ester" and "boronic ester" are used interchangeably and refer to a chemical compound containing a —B($Z^1$)($Z^2$) moiety, wherein at least one of $Z^1$ or $Z^2$ is alkoxy, aralkoxy, or aryloxy; or $Z^1$ and $Z^2$ together form a moiety derived from a boronic acid complexing agent having at least one hydroxyl group.

In some embodiments, $Z^1$ and $Z^2$ together form a moiety derived from a compound having at least two hydroxyl groups separated by at least two connecting atoms in a chain or ring, said chain or ring comprising carbon atoms and, optionally, a heteroatom or heteroatoms which can be N, S, or O, wherein the atom attached to boron in each case is an oxygen atom.

As employed herein, the term "compound having at least two hydroxyl groups" refers to any compound having two or more hydroxyl groups. For purposes of the invention, the two hydroxyl groups preferably are separated by at least two connecting atoms, preferably from about 2 to about 5 connecting atoms, more preferably 2 or 3 connecting atoms. For convenience, the term "dihydroxy compound" may be used to refer to a compound having at least two hydroxyl groups, as defined above. Thus, as employed herein, the term "dihydroxy compound" is not intended to be limited to compounds having only two hydroxyl groups. The moiety derived from a compound having at least two hydroxyl groups may be attached to boron by the oxygen atoms of any two of its hydroxyl groups. Preferably, the boron atom, the oxygen atoms attached to boron, and the atoms connecting the two oxygen atoms together form a 5- or 6-membered ring.

For purposes of the present invention, the boronic acid complexing agent preferably is pharmaceutically acceptable, i.e., suitable for administration to humans. In some preferred embodiments, the boronic acid complexing agent is a sugar. The term "sugar" includes any polyhydroxy carbohydrate moiety, including monosaccharides, disaccharides, polysaccharides, sugar alcohols and amino sugars. In some embodiments, the sugar is a monosaccharide, disaccharide, sugar alcohol, or amino sugar. Non-limiting examples of suitable sugars include glucose, sucrose, fructose, trehalose, mannitol, sorbitol, glucosamine, and N-methylglucosamine. In certain embodiments, the sugar is mannitol or sorbitol. Thus, in the embodiments wherein the sugar is mannitol or sorbitol, $Z^1$ and $Z^2$ together form a moiety of formula $C_6H_{12}O_6$, wherein the oxygen atoms of the two deprotonated hydroxyl groups form covalent attachments with boron to form a boronate ester compound. In certain particular embodiments, $Z^1$ and $Z^2$ together form a moiety derived from D-mannitol.

In some embodiments, the compound of formula (I) is formulated as a lyophilized powder, as described in Plamondon et al., WO 02/059131, hereby incorporated by reference in its entirety. In some embodiments, the lyophilized powder also comprises free dihydroxy compound. Preferably, the free dihydroxy compound and the compound of formula (I) are present in the mixture in a molar ratio ranging from about 0.5:1 to about 100:1, more preferably from about 5:1 to about 100:1. In various embodiments wherein the dihydroxy compound is mannitol, the lyophilized powder comprises free mannitol and mannitol boronate ester in a molar ratio ranging from about 10:1 to about 100:1, from about 20:1 to about 100:1, or from about 40:1 to about 100:1.

In some embodiments, the lyophilized powder comprises mannitol and a compound of formula (I), substantially free of other components. However, the composition can further comprise one or more other pharmaceutically acceptable excipients, carriers, diluents, fillers, salts, buffers, stabilizers, solubilizers, and other materials well known in the art. The preparation of pharmaceutically acceptable formulations containing these materials is described in, e.g., *Remington: The Science and Practice of Pharmacy*, 20th Ed., ed. A. Gennaro, Lippincott Williams & Wilkins, 2000, or latest edition.

The lyophilized powder comprising the compound of formula (I) preferably is prepared according to the procedures described in Plamondon et al., WO 02/059131. Thus, in some embodiments, the method for preparing the lyophilized powder comprises: (a) preparing an aqueous mixture comprising a peptide boronic acid and a dihydroxy compound; and (b) lyophilizing the mixture.

General Synthetic Methodology

The compounds of formula (I) can be prepared by methods known to one of ordinary skill in the art. See, e.g., Adams et. al., U.S. Pat. No. 5,780,454; Pickersgill et al., International Patent Publication WO 2005/097809. An exemplary synthetic route is set forth in Scheme 1 below.

Scheme 1:

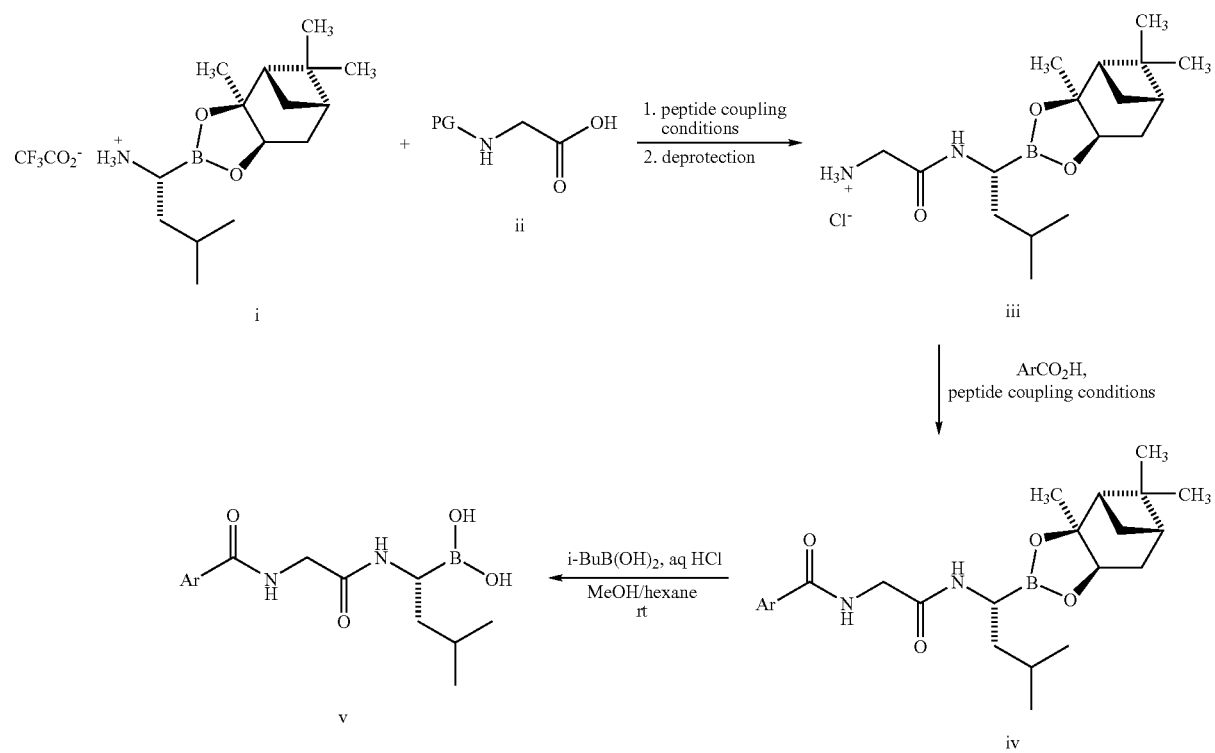

Coupling of compound i with an N-protected glycine (ii), followed by N-terminal deprotection, provides compound iii. Examples of suitable protecting groups (PG) include, without limitation, acyl protecting groups, e.g., formyl, acetyl (Ac), succinyl (Suc), and methoxysuccinyl; and urethane protecting groups, e.g., tert-butoxycarbonyl (Boc), benzyloxycarbonyl (Cbz), and fluorenylmethoxycarbonyl (Fmoc). The peptide coupling reaction can be conducted by prior conversion of the carboxylic acid moiety of compound ii to an activated ester, e.g., an O-(N-hydroxysuccinnimide) ester, followed by treatment with compound i. Alternatively, the activated ester can be generated in situ by contacting the carboxylic acid with a peptide coupling reagent. Examples of suitable peptide coupling reagents include, without limitation, carbodiimide reagents, e.g., dicyclohexylcarbodiimide (DCC) or 1-(3-dimethylaminopropyl)-3-ethylcarbodiimide (EDC); phosphonium reagents, e.g., benzotriazol-1-yloxytris(dimethylamino)phosphonium hexafluorophosphate (BOP); and uranium reagents, e.g., O-(1H-benzotriazol-1-yl)-N,N,N',N'-tetramthyluronium tetrafluoroborate (TBTU).

Compound iii is then coupled with a substituted benzoic acid (ArCO₂H) to afford compound iv. The peptide coupling conditions described above for the coupling of compounds i and ii are also suitable for coupling compound iii with ArCO₂H. Deprotection of the boronic acid moiety then affords compound v. The deprotection step preferably is accomplished by transesterification in a biphasic mixture comprising the boronic ester compound iv, an organic boronic acid acceptor, a lower alkanol, a $C_{5-8}$ hydrocarbon solvent, and aqueous mineral acid.

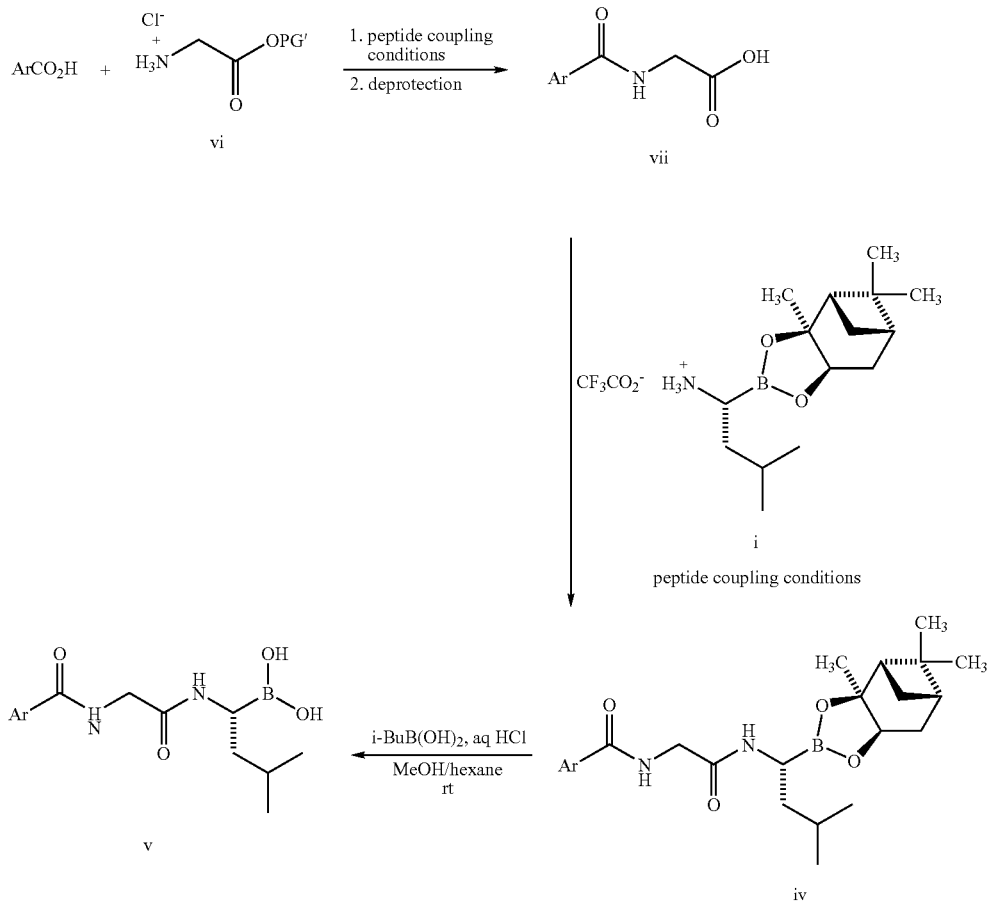

Scheme 2:

Alternatively, the order of coupling reactions can be reversed, as shown in Scheme 2. Thus, an O-protected glycine (vi) is first coupled with a substituted benzoic acid (ArCO₂H), followed by ester hydrolysis, to form compound vii. Coupling with compound i and boronic acid deprotection are then accomplished as described above for Scheme 1 to afford compound v.

Uses, Formulation, and Administration

The present invention provides compounds that are potent inhibitors of the proteasome. The compounds can be assayed in vitro or in vivo for their ability to inhibit proteasome-mediated peptide hydrolysis or protein degradation.

In another aspect, therefore, the invention provides a method for inhibiting one or more peptidase activities of a proteasome in a cell, comprising contacting a cell in which proteasome inhibition is desired with a compound described herein, or a pharmaceutically acceptable salt, boronic ester, or boronic acid anhydride thereof.

The invention also provides a method for inhibiting cell proliferation, comprising contacting a cell in which such inhibition is desired with a compound described herein. The phrase "inhibiting cell proliferation" is used to denote the ability of a compound of the invention to inhibit cell number or cell growth in contacted cells as compared to cells not contacted with the inhibitor. An assessment of cell proliferation can be made by counting cells using a cell counter or by an assay of cell viability, e.g., an MTT or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, a proteasome inhibitor that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I), or a pharmaceutically acceptable salt or boronic acid anhydride thereof, and a pharmaceutically acceptable carrier.

If a pharmaceutically acceptable salt of the compound of the invention is utilized in these compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as lithium, sodium and potassium salts; alkaline earth metal salts, such as calcium and magnesium salts; other multivalent metal salts, such as zinc salts; salts with organic bases, such as dicyclohexylamine, N-methyl-D-glucamine, t-butylamine, ethylene diamine, ethanolamine, and choline; and salts with amino acids such as arginine, lysine, and so forth. In some embodiments, the pharmaceutically acceptable salt is a base addition salt of a boronic acid compound of formula (I), wherein $Z^1$ and $Z^2$ are both hydroxy.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, pH modifiers, isotonic agents, thickening or emulsifying agents, preservatives, solid binders, lubricants and the like, as suited to the particular dosage form desired. *Remington: The Science and Practice of Pharmacy,* 20th Ed., ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, carbonates, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, and mannitol, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins such as hydroxypropyl β-cyclodextrin and sulfobutylether β-cyclodextrin, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the compound of formula (I) is administered intravenously. In such embodiments, the compound of formula (I) wherein $Z^1$ and $Z^2$ together form a moiety derived from a boronic acid complexing agent can be prepared in the form of a lyophilized powder, as described above. The lyophilized powder preferably is reconstituted by adding an aqueous solvent suitable for pharmaceutical administrations. Examples of suitable reconstitution solvents include, without limitation, water, saline, and phosphate buffered saline (PBS). Preferably, the lyophilized powder is reconstituted with normal (0.9%) saline. Upon reconstitution, an equilibrium is established between a boronate ester compound and the corresponding free boronic acid compound. In some embodiments, equilibrium is reached quickly, e.g., within 10-15 minutes, after the addition of aqueous medium. The relative concentrations of boronate ester and boronic acid present at equilibrium is dependent upon parameters such as, e.g., the pH of the solution, temperature, the nature of the boronic acid complexing agent, and the ratio of boronic acid complexing agent to boronate ester compound present in the lyophilized powder.

The pharmaceutical compositions of the invention preferably are formulated for administration to a patient having, or at risk of developing or experiencing a recurrence of, a proteasome-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. In some embodiments, such other therapeutic agent is one that is normally administered to patients with the disease or condition being treated.

By "therapeutically effective amount" is meant an amount sufficient to cause a detectable decrease in proteasome activity or the severity of a proteasome-mediated disorder. The amount of proteasome inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having, or at risk of developing or experiencing a recurrence of, a proteasome-mediated disorder. As used herein, the term "proteasome-mediated disorder" includes any disorder, disease or condition which is caused or characterized by an increase in proteasome expression or activity, or which requires proteasome activity. The term "proteasome-mediated disorder" also includes any disorder, disease or condition in which inhibition of proteasome activity is beneficial.

For example, compounds and pharmaceutical compositions of the invention are useful in treatment of disorders mediated via proteins (e.g., NFκB, p27$^{Kip}$, p21$^{WAF/CIP1}$, p53) which are regulated by proteasome activity. Relevant disorders include inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis)), vascular proliferative disorders (e.g., atherosclerosis, restenosis), proliferative ocular disorders (e.g., diabetic retinopathy), benign proliferative disorders (e.g., hemangiomas), autoimmune diseases (e.g., multiple sclerosis, tissue and organ rejection), as well as inflammation associated with infection (e.g., immune responses), neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed proteasome inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed proteasome inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the compound or composition of the invention is used to treat a patient having or at risk of developing or experiencing a recurrence in a cancer selected from the group consisting of multiple myeloma and mantle cell lymphoma.

In some embodiments, the proteasome inhibitor of the invention is administered in conjunction with another therapeutic agent. The other therapeutic agent may also inhibit the proteasome, or may operate by a different mechanism. In some embodiments, the other therapeutic agent is one that is normally administered to patients with the disease or condition being treated. The proteasome inhibitor of the invention may be administered with the other therapeutic agent in a single dosage form or as a separate dosage form. When administered as a separate dosage form, the other therapeutic agent may be administered prior to, at the same time as, or following administration of the proteasome inhibitor of the invention.

In some embodiments, a proteasome inhibitor of formula (I) is administered in conjunction with an anticancer agent. As used herein, the term "anticancer agent" refers to any agent that is administered to a subject with cancer for purposes of treating the cancer.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In order that this invention be more fully understood, the following preparative and testing examples are set forth. These examples illustrate how to make or test specific compounds, and are not to be construed as limiting the scope of the invention in any way.

EXAMPLES

| | Abbreviations |
|---|---|
| DCM | methylene chloride |
| DIEA | diisopropylethyl amine |
| EDCI | N-(3-dimethylaminopropyl)-N'-ethylcarbodiimide hydrochloride |
| EtOAc | ethyl acetate |
| h | hours |
| HPLC | high performance liquid chromatography |
| TBTU | o-benzotriazol-1-yl-N,N,N',N'-tetramethyluronium tetrafluoroborate |
| HOBt | 1-hydroxybenztriazole hydrate |
| LCMS | liquid chromatography mass spectrum |
| min | minutes |
| tr | retention time from diode array spectra |

Analytical LC-MS Methods

Spectra were run on a Symmetry C18-3.5 μm-4.6×50 mm column using the following gradient:

Solvent A: 2% isopropyl alcohol, 98% water, 10 mM NH4OAc

Solvent B: 75% acetonitrile, 25% methanol, 10 mM NH4OAc

| Time [min] | Flow rate [mL/min] | % of solvent B |
|---|---|---|
| 0.0 | 1.0 | 5.0 |
| 3.5 | 1.0 | 100.0 |
| 4.9 | 1.0 | 100.0 |
| 5.0 | 1.0 | 5.0 |

Example 1

Synthesis of [(1R)-1-({[(2,3-difluorobenzoyl)amino]acetyl}amino)-3-methylbutyl]boronic acid.20 D-mannitol (I-1)

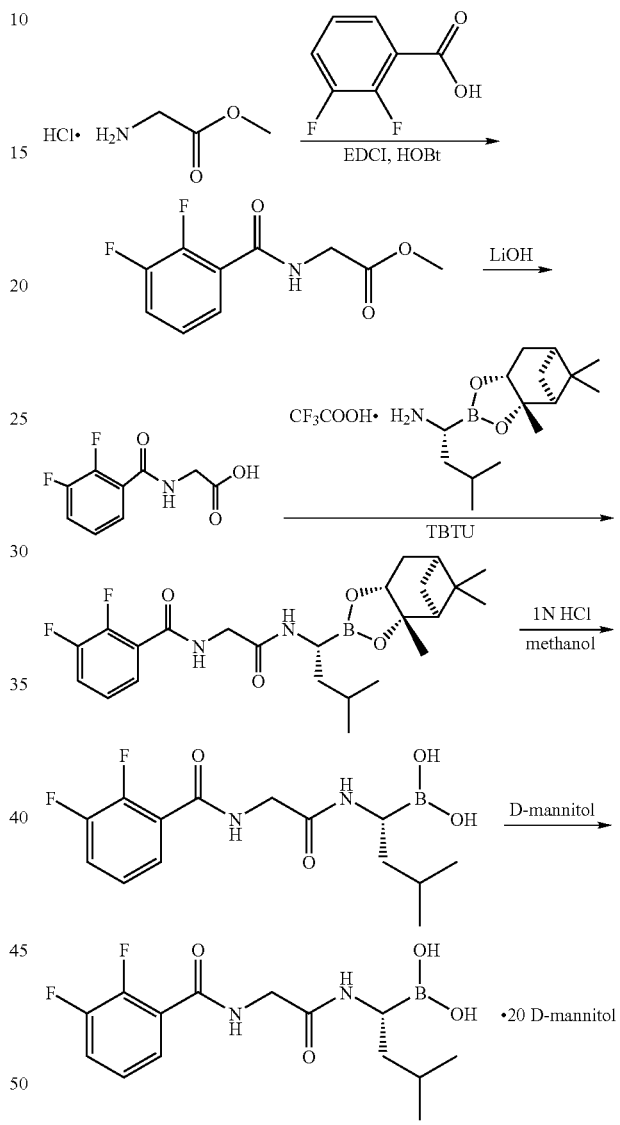

Step 1: methyl [(2,3-difluorobenzoyl)amino]acetate

To a solution of 2,3-difluorobenzoic acid (0.190 g, 1.2 mmol) in tetrahydrofuran (5 mL) were added glycine methyl ester hydrochloride (0.150 g, 1.2 mmol), HOBt (0.162 g, 1.2 mmol), DIEA (0.209 mL, 1.2 mmol) and EDCI (0.252 g, 1.3 mmol). The reaction mixture was allowed to stir overnight. The reaction mixture was quenched with a saturated solution of sodium bicarbonate and the product partitioned into DCM. Separation of the organic layer followed by removal of the solvent gave methyl [(2,3-difluorobenzoyl)amino]acetate which was used in the next step without purification.

Step 2: [(2,3-difluorobenzoyl)amino]acetic acid

To a solution of methyl [(2,3-difluorobenzoyl)amino]acetate (0.250 g, 1.1 mmol) in methanol (7 mL) were added lithium hydroxide (0.053 g, 2.2 mmol) and water (3 mL). The reaction mixture was allowed to stir overnight. The mixture was diluted with water (20 mL) and acidified with 1N HCl (5 mL). The product was partitioned into DCM/methanol (4:1). The organic layer was dried over sodium sulfate and the solvent removed to give [(2,3-difluorobenzoyl)amino]acetic acid which was used in the next step without purification.

Step 3: 2,3-difluoro-N-[2-({(1R)-3-methyl-1-[(3aR,4R,6R,7aS)-3a,5,5-trimethylhexahydro-4,6-methano-1,3,2-benzodioxaborol-2-yl]butyl}amino)-2-oxoethyl]benzamide To a solution of [(2,3-difluorobenzoyl)amino]acetic acid (0.205 g, 0.95 mmol) in dimethylformamide (10 mL) were added TBTU (0.337 g, 1.0 mmol) and (1R)-3-methyl-1-[(3aS,4S,6S,7aR)-3a,5,5-trimethylhexahydro-4,6-methano-1,3,2-benzodioxaborol-2-yl]butan-1-amine as its trifluoroacetate salt (0.362 g, 0.95 mmol). The mixture was allowed to cool to 0° C. and DIEA (0.498 mL, 2.9 mmol) was added dropwise. The reaction mixture was allowed to warm to room temperature and stirred overnight. The reaction was quenched with water (100 mL) and the product partitioned into DCM. The organic layer was dried over sodium sulfate and the solvent removed to give 2,3-difluoro-N-[2-({(1R)-3-methyl-1-[(3aR,4R,6R,7aS)-3a,5,5-trimethylhexahydro-4,6-methano-1,3,2-benzodioxaborol-2-yl]butyl}amino)-2-oxoethyl]benzamide.

Step 4: [(1R)-1-({[(2,3-difluorobenzoyl)amino]acetyl}amino)-3-methylbutyl]boronic acid To a solution of 2,3-difluoro-N-[2-({(1R)-3-methyl-1-[(3aR,4R,6R,7aS)-3a,5,5-trimethylhexahydro-4,6-methano-1,3,2-benzodioxaborol-2-yl]butyl}amino)-2-oxoethyl]benzamide (0.536 g, 1.2 mmol) in methanol/1N HCl (1:1) (1.5 mL) were added heptanol (1 mL) and isobutyl boronate (0.207 g, 2.0 mmol). The reaction mixture was allowed to stir overnight. The heptanol layer was separated and the methanol/HCl layer was concentrated. The crude product was purified by reverse phase HPLC to give [(1R)-1-({[(2,3-difluorobenzoyl)amino]acetyl}amino)-3-methylbutyl]boronic acid.

Step 5: [(1R)-1-({[2,3-difluorobenzoyl)amino]acetyl}amino)-3-methylbutyl]boronic acid.20 D-mannitol (I-1)

To a solution of [(1R)-1-({[(2,3-difluorobenzoyl)amino]acetyl}amino)-3-methylbutyl]boronic acid (0.085 g, 0.26 mmol) in t-butyl alcohol (2 mL) and water (5 mL) was added D-mannitol (0.943 g, 5.2 mmol). The solution was warmed and allowed to stir until everything dissolved. The solution was then frozen and the solvent removed by lyophilization to give [(1R)-1-({[(2,3-difluorobenzoyl)amino]acetyl}amino)-3-methylbutyl]boronic acid.20 D-mannitol (I-1) (0.98 g, 97%).

Example 2

Synthesis of [(1R)-1-({[(2-bromobenzoyl)amino]acetyl}amino)-3-methylbutyl]boronic acid.20 D-mannitol (I-5)

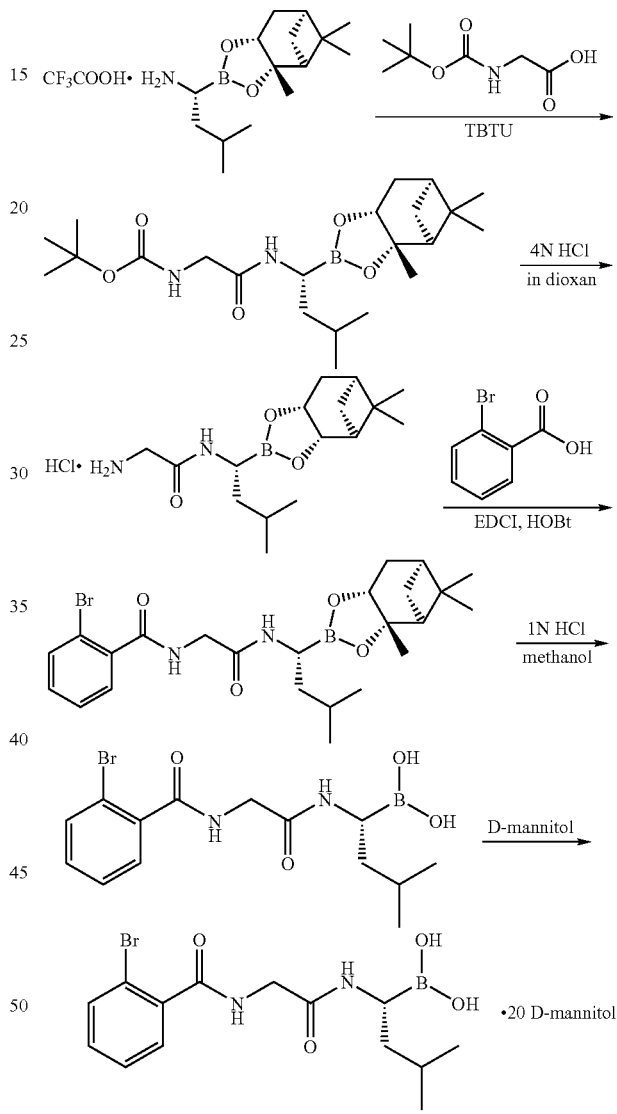

Step 1: tert-butyl [2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]carbamate To a mixture of (1R)-3-methyl-1-[(3aS,4S,6S,7aR)-3a,5,5-trimethylhexahydro-4,6-methano-1,3,2-benzodioxaborol-2-yl]butan-1-amine as its trifluoroacetate salt (4.9 g, 10.8 mmol), N-•-(tert-Butoxycarbonyl)glycine (1.98 g, 11.3 mmol) and TBTU (3.81 g, 11.9 mmol) in DCM (100 mL) was added dropwise over 15 min a solution of DIEA (5.64 mL, 32.4 mmol) in DCM (25 mL). The reaction mixture was allowed to stir overnight and was concentrated. The crude product was purified by column chromatography to give tert-butyl [2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]carbamate (2.5 g, 55%).

Step 2: 2-amino-N-{(1R)-3-methyl-1-[(3aS,4S,6S,7aR)-3a,5,5-trimethylhexahydro-4,6-methano-1,3,2-benzodioxaborol-2-yl]butyl}acetamide To a solution of tert-butyl [2-({(1R)-3-methyl-1-[(3aS,6S,7aR)-3a,5,5-trimethylhexahydro-4,6-methano-1,3,2-benzodioxaborol-2-yl]butyl}amino)-2-oxoethyl]carbamate (2.5 g, 5.9 mmol) in DCM (15 mL) was added 4M HCl in dioxane (5.9 mL). The reaction mixture was allowed to stir for 2 h and concentrated to give 2-amino-N-{(1R)-3-methyl-1-[(3aS,4S,6S,7aR)-3a,5,5-trimethylhexahydro-4,6-methano-1,3,2-benzodioxaborol-2-yl]butyl}acetamide which was used in the next step without purification.

Step 3: 2-bromo-N-[2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]benzamide To a solution of 2-bromobenzoic acid (0.124 g, 0.62 mmol) in DCM (2.25 mL) were added EDCI (0.119 g, 0.62 mmol), HOBt (0.084 g, 0.62 mmol), N-methyl morpholine (0.185 mL, 1.68 mmol) and 2-amino-N-{(1R)-3-methyl-1-[(3aS,4S,6S,7aR)-3a,5,5-trimethylhexahydro-4,6-methano-1,3,2-benzodioxaborol-2-yl]butyl}acetamide (0.2 g, 0.56 mmol). The reaction mixture was allowed to stir for 2 h and was concentrated. The residue was diluted with water and extracted with EtOAc. The organic solutions were combined, washed with brine, dried over $MgSO_4$, filtered and concentrated. The crude product was purified by column chromatography to give 2-bromo-N-[2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]benzamide (0.22 g, 78%).

Step 4: [(1R)-1-({[(2-bromobenzoyl)amino]acetyl}amino)-3-methylbutyl]boronic acid To a solution of 2-bromo-N-[2-({(1R)-3-methyl-1-[(3aS,4S,6S,7aR)-3a,5,5-trimethylhexahydro-4,6-methano-1,3,2-benzodioxaborol-2-yl]butyl}amino)-2-oxoethyl]benzamide (0.220 g, 0.44 mmol) in methanol/hexane (1:1) (2.2 mL) were added 1N HCl (1 mL, 1.0 mmol) and isobutyl boronate (0.078 g, 0.76 mmol). The reaction mixture was allowed to stir overnight. The reaction mixture was concentrated and purified by reverse phase HPLC to give [(1R)-1-({[(2-bromobenzoyl)amino]acetyl}amino)-3-methylbutyl]boronic acid (0.119 g, 73%).

Step 5: [(1R)-1-({[(2-bromobenzoyl)amino]acetyl}amino)-3-methylbutyl]boronic acid.20 D-mannitol (I-5)

To a solution of [(1R)-1-({[(2-bromobenzoyl)amino]acetyl}amino)-3-methylbutyl]boronic acid (0.103 g, 0.28 mmol) in tent-butyl alcohol (9 mL) and water (15 mL) was added D-mannitol (1.01 g, 5.5 mmol). The solution was warmed and allowed to stir until everything dissolved. The solution was then frozen and the solvent removed by lyophilization to give [(1R)-1-({[(2-bromobenzoyl)amino]acetyl}amino)-3-methylbutyl]boronic acid.20 D-mannitol (I-5) (0.92 g, 84%).

Compounds in the following table were prepared from the appropriate starting materials in a method analogous to that of Example 1 or 2:

| | |
|---|---|
| I-1 | LCMS: ES– 327.3, tr = 3.36 min. |
| I-2 | LCMS: ES– 343.2, tr = 3.62 min. |
| I-3 | LCMS: ES– 327.3, tr = 3.49 min. |
| I-4 | LCMS: ES– 327.2, tr = 3.27 min. |
| I-5 | LCMS: ES– 369.2, tr = 3.30 min.<br>$^1$H NMR (300 MHz, $d_4$-MeOD) δ: 7.62 (dd, 1H), 7.28-7.50 (m, 3H), 4.19 (s, 2H), 2.70-2.78 (m, 1H), 1.57-1.71 (m, 1H), 1.26-1.40 (m, 2H) and 0.89 (d, 6H). |
| I-6 | LCMS: ES– 309.1, tr = 3.14 min. |
| I-7 | LCMS: ES– 343.2, tr = 3.30 min. |
| I-8 | LCMS: ES– 309.3, tr = 3.23 min. |
| I-9 | LCMS: ES– 327.3, tr = 3.49 min. |
| I-10 | LCMS: ES– 325.2, tr = 3.58 min. |
| I-11 | LCMS: ES– 359.2, tr = 3.66 min.<br>$^1$H NMR (300 MHz, $d_4$-MeOD) δ: 7.62 (s, 1H), 7.49 (d, 2H), 4.23 (s, 2H), 2.74-2.82 (m, 1H), 1.62-1.78 (m, 1H), 1.30-1.45 (m, 2H) and 0.95 (d, 6H). |
| I-12 | LCMS: ES– 359.2, tr = 3.95 min. |
| I-13 | LCMS: ES– 309.2, tr = 3.34 min. |
| I-14 | LCMS: ES– 343.2, tr = 3.44 min. |
| I-15 | LCMS: ES– 359.2, tr = 3.26 min. |
| I-16 | LCMS: ES– 325.2, tr = 3.20 min. |
| I-17 | LCMS: ES– 327.3, tr = 3.39 min. |
| I-18 | LCMS: ES– 343.2, tr = 3.58 min. |
| I-19 | LCMS: ES– 325.1, tr = 3.51 min. |
| I-20 | LCMS: ES– 359.2, tr = 3.54 min. |
| I-21 | LCMS: ES– 359.2, tr = 3.99 min. |

Example 2

20S Proteasome Assay

To 1 µL of test compound dissolved in DMSO in a 384-well black microtiter plate is added 25 µL of assay buffer at 37° C. containing human PA28 activator (Boston Biochem, 12 nM final) with Ac-WLA-AMC (β5 selective substrate) (15 µM final), followed by 25 µL of assay buffer at 37° C. containing human 20S proteasome (Boston Biochem, 0.25 nM final). Assay buffer is composed of 20 mM HEPES, 0.5 mM EDTA and 0.01% BSA, pH7.4. The reaction is followed on a BMG Galaxy plate reader (37° C., excitation 380 nm, emission 460 nm, gain 20). Percent inhibition is calculated relative to 0% inhibition (DMSO) and 100% inhibition (10 µM bortezomib) controls.

When tested in this assay, compounds I-1 to I-21 all exhibited $IC_{50}$ values less than 50 nM.

Example 3

Antiproliferation Assay

HCT-116 (1000) or other tumor cells in 100 µL of appropriate cell culture medium (McCoy's 5A for HCT-116, Invitrogen) supplemented with 10% fetal bovine serum (Invitrogen) are seeded in wells of a 96-well cell culture plate and incubated overnight at 37° C. Test compounds are added to the wells and the plates are incubated for 96 hours at 37° C. MTT or WST reagent (10 µL, Roche) are added to each well and incubated for 4 hours at 37° C. as described by the manufacturer. For MTT the metabolized dye is solubilized overnight according to manufacturer's instructions (Roche).

The optical density for each well is read at 595 nm (primary) and 690 nm (reference) for the MTT and 450 nm for the WST using a spectrophotometer (Molecular Devices). For the MTT the reference optical density values are subtracted from the values of the primary wavelength. Percent inhibition is calculated using the values from a DMSO control set to 100%.

Example 4

In Vivo Tumor Efficacy Model

Freshly dissociated HCT-116 ($2\text{-}5\times10^6$) or other tumor cells in 100 μL of RPMI-1640 media (Sigma-Aldrich) are aseptically injected into the subcutaneous space in the right dorsal flank of female CD-1 nude mice (age 5-8 weeks, Charles River) using a 1 mL 26⅜-ga needle (Becton Dickinson Ref#309625). Alternatively, some xenograft models require the serial passaging of tumor fragments. In these cases, small fragments of tumor tissue (approximately 1 mm$^3$) are implanted subcutaneously in the right dorsal flank of anesthetized (3-5% isoflourane/oxygen mixture) C.B-17/SCID mice (age 5-8 weeks, Charles River) via a 13-ga trocar (Popper & Sons 7927). Beginning at day 7 after inoculation tumors are measured twice weekly using a vernier caliper. Tumor volumes are calculated using standard procedures ($0.5\times(\text{length}\times\text{width}^2)$). When the tumors reach a volume of approximately 200 mm$^3$ mice are randomized into treatment groups and begin receiving drug treatment. Dosing and schedules are determined for each experiment based on previous results obtained from pharmacokinetic/pharmacodynamic and maximum tolerated dose studies. The control group will receive vehicle without any drug. Typically, test compound (100-200 μL) is administered via intravenous (27-ga needle), oral (20-ga gavage needle) or subcutaneous (27-ga needle) routes at various doses and schedules. Tumor size and body weight are measured twice a week and the study is terminated when the control tumors reach approximately 2000 mm$^3$.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A compound of formula (I):

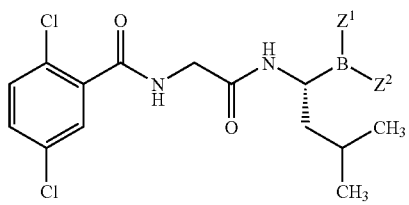

wherein:
$Z^1$ and $Z^2$ together form a moiety derived from a boronic acid complexing agent.

2. A pharmaceutical composition comprising a compound of claim 1 and a pharmaceutically acceptable carrier.

3. A method of treating cancer, comprising administering to a patient in need of such treatment a pharmaceutical composition according to claim 2.

* * * * *